United States Patent [19]

Blum

[11] 4,254,084
[45] Mar. 3, 1981

[54] METHOD AND APPARATAUS FOR AUTOMATIC ISOENZYME ANALYSIS

[76] Inventor: Alvin S. Blum, 2350 Del Mar Place, Fort Lauderdale, Fla. 33301

[21] Appl. No.: 968,907

[22] Filed: Dec. 13, 1978

Related U.S. Application Data

[63] Continuation-in-part of Ser. No. 898,998, Apr. 21, 1978.

[51] Int. Cl.³ .................. G01N 33/56; G01N 35/08; G01N 21/05
[52] U.S. Cl. .................. 422/81; 23/230 B; 204/180 G; 356/246; 422/82; 435/291
[58] Field of Search ........... 204/180 G; 356/197, 356/246; 23/230 R, 230 B; 422/81, 82, 72; 435/291

[56] References Cited
U.S. PATENT DOCUMENTS

| 3,795,451 | 3/1974 | Mailen | 422/72 |
| 3,801,283 | 4/1972 | Shapiro et al. | 422/72 |
| 3,829,223 | 8/1974 | Hamel | 422/72 |
| 3,864,089 | 2/1975 | Tiffany et al. | 422/72 |
| 4,030,834 | 6/1977 | Bauer et al. | 422/72 |

*Primary Examiner*—Ronald Serwin

[57] ABSTRACT

Continuous enzyme analyzer including dispensing of samples, reagents, and wash liquid, and separation of certain molecules into multiple individual streams, and optical flow cell for serial measurements of those multiple streams at progressively greater time intervals. Serial temperature adjustment of the streams to conserve reagents. Improved optical cell structure intergrating mixing, temperature control, and multiple optical flow paths each providing sensing of a portion of the stream at progressively greater time intervals in a single laminated apparatus.

21 Claims, 14 Drawing Figures

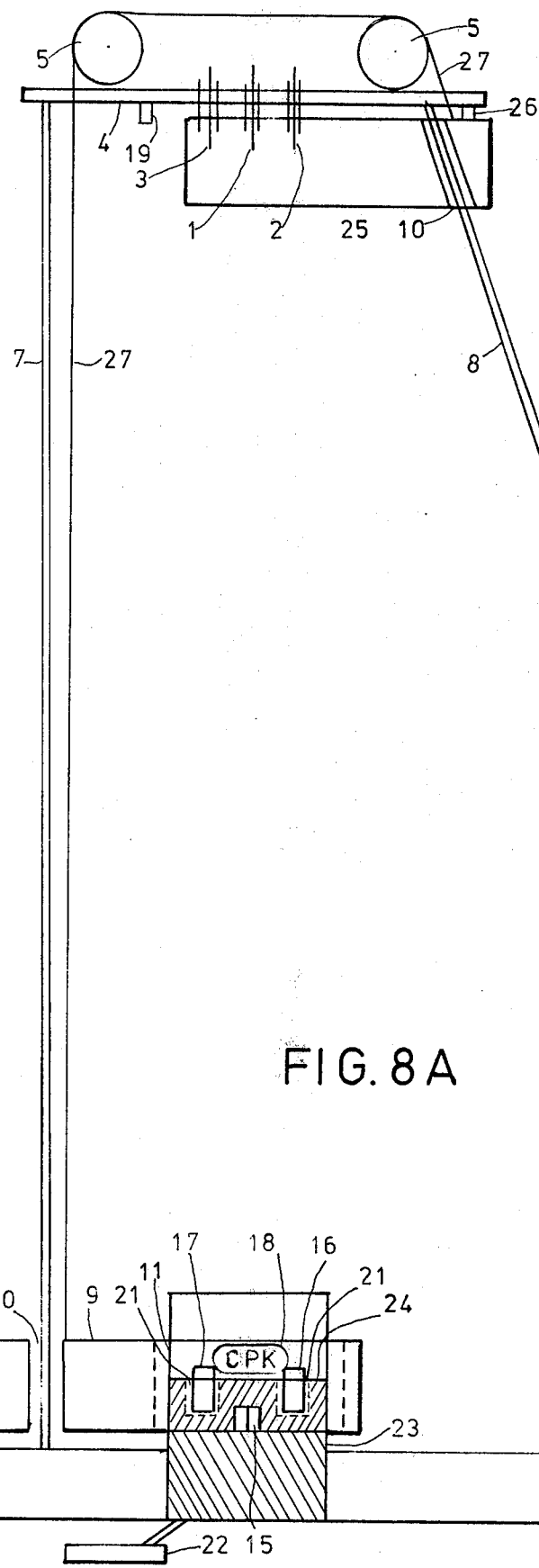
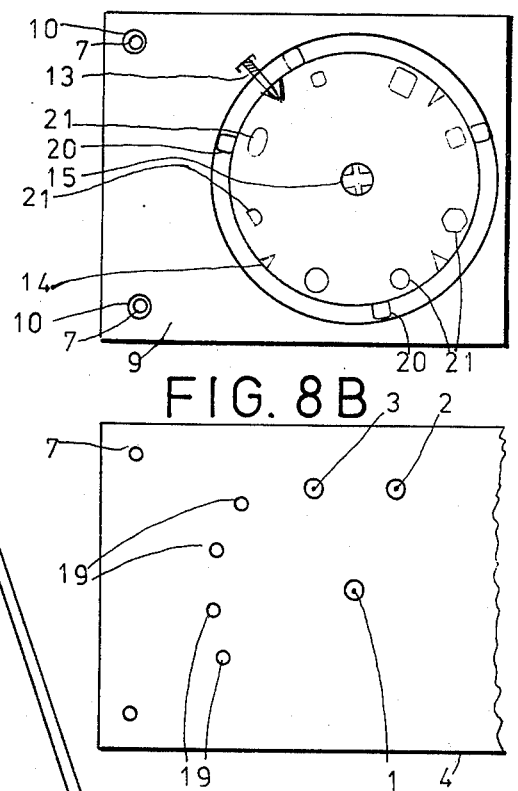
FIG. 8B
FIG. 8C
FIG. 8A

METHOD AND APPARATAUS FOR AUTOMATIC ISOENZYME ANALYSIS

This is a continuation-in-part of application Ser. No. 898,998, filed Apr. 21, 1978.

BACKGROUND OF THE INVENTION

1. Field of the Invention

The invention relates to a method and apparatus for analyzing isoenzymes. Isoenzymes are multiple molecular forms of an enzyme which catalyze the same reaction, but differ in certain physical chemical properties, such as electrophoretic mobility. Following electrophoresis five isoenzymes of lactic dehydrogenase (LDH) and three isoenzymes of creatine phosphokinase (CPK) have been demonstrated in human serum. Each isoenzyme of LDH is designated by a number related to its electrophoretic mobility. The fastest moving fraction (most anodic) is designated LDH1 and is found primarily in heart muscle. The slowest moving (most cathodic) is LDH5 and is found primarily in liver and skeletal muscle. The others LDH2, LDH3 and LDH4 are found to varying degrees along with LDH1 and LDH5 in all tissues.

The multiple forms of CPK demonstrated after electrophoresis are due to the fact that CPK is a dimer (two polypeptide chains). Both polypeptide chains of skeletal muscle CPK are the same and have been designated MM. Brain CPK, identified as BB, contains two identical polypeptide chains, but they differ from the polypeptide chains of MM. Heart muscle CPK contains one skeletal muscle and one brain polypeptide chain and is designated MB. During electrophoresis, BB moves fastest and is found closest to the anode. MM moves slowest and is found closest to the cathode. MB moves in between. The most important current clinical application for isoenzyme analysis is to confirm or rule out the diagnosis of acute myocardial infarction. A patient admitted to the hospital with chest pains should have CPK and LDH isoenzyme analyses run immediately upon admission. Another assay should be performed within 6-13 hours and 24-37 hours. If an increased CPK MB level cannot be demonstrated during this period, there is about a 100% certainty that the patient didn't sustain a myocardial infarct for the episode in question.

Normally, LDH2 is greater than LDH1. Following myocardial infarct, LDH1 increases, resulting in LDH1 becoming greater than LDH2. This is referred to as a "flipped LDH ratio". This occurs in 80% of all myocardial infarcts in 48 hours. The presence of an increased CPK MB and a flipped LDH ratio within the first 48 hours is almost 100% indicative of a myocardial infarction. Increased CPK MB and normal LDH may indicate intermediate syndrome, coronary insufficiency, or crescendo angina as well as myocardial infarct. Other measures, such as EKG must then be considered to establish the diagnosis.

2. Description of the Prior Art

Enzyme analyses are generally performed in solution by spectrophotometric or fluorometric measurements under controlled conditions of the disappearance or appearance of a substrate or its metabolite. Isoenzymes can be separated by column chromatography and the enzyme concentration of the eluates determined by such means. However these procedures have been shown to have poor precision and accuracy and to be fraught with problems of interpretation. They are also time consuming. In current clinical practice, isoenzymes are generally analyzed by first performing electrophoretic separation of the serum on a cellulose acetate or agarose support strip in an electric field in a suitable buffer for 10 minutes. The strip containing the separated isoenzymes is then sandwiched against a second strip holding the appropriate reagents to visualize either CPK or LDH after 25 minutes incubation. The strip is then dried and quantitated by a scanning fluorescent densitometer. 13 (CPK) or 20 (LDH) individual skilled steps are necessary before the strip is ready for the densitometer. The automatic densitometer costs $3750 to $6000 and a computer to assist its somewhat complex operation costs at least $3000. A considerable effort and time of a skilled operator is required for these densitometric measurements.

There may be other interfering enzymes or agents in the serum which may react to give false readings of the desired enzyme. It is expected that other isoenzyme analyses may prove useful in the future when suitable methods and data become available.

It is difficult to provide at all hours the skilled staff required to perform these analyses. With all the other duties charged to the laboratorian, such time consuming procedures cannot be performed on the stat basis that many patients' condition dictates. The present procedures are so awkward and involve so many steps and variables that they are quite imprecise even in the best of hands. A need exists for a technique which completes automation with simplicity, versatility, precision, and rapid throughput for stat samples that will be available for use by relatively unskilled persons at all hours with little operator time.

SUMMARY OF THE PRESENT INVENTION

One object of the present invention is to provide an apparatus and method for automatic isoenzyme analysis that is simple to operate, relatively foolproof, reliable, consistent, direct reading, fast action, conservative of expensive reagents, available at all hours, fast easy changeover from one enzyme to another so that on a single sample it becomes practical to perform CPK and then LDH instead of batching multiple samples and running CPK on all of them and then changing to LDH. It is a further object of the invention that new enzyme assays are easily added to the repertory. It is a further object that automatic means be provided for removing interfering materials from the sample to improve enzyme analysis. It is a further object that means be provided for separating the isoenzymes into separate moving streams. It is a further object that means be provided for admixing reagents with said streams of separated enzymes. It is a further object that means be provided to control temperature of said mixtures. It is a further object that means be provided to measure changes in optical properties of said mixtures. It is a further object that data processing means be provided to convert optical measurements into useful data readout. It is a further object of the invention that it provide a wide range of sensitivities so that very low values can be measured and very high values can also be measured before reagent is exhausted and require dilution and repeat analysis.

Another object of the present invention is to provide novel method and apparatus for the separation, in a moving fluid stream, of a particular type of molecule from other types of molecules on the basis of certain differences in their physical chemical properties. This invention provides simple and inexpensive electroextraction means to separate said molecules which comprises: a central channel through which flows the mixture of molecules to be separated; at least one additional parallel recipient flow channel adjacent the central channel and separated therefrom along its greater length by a membrane sufficiently permeable to allow passage of at least one of the types of molecules to be separated; electrodes in at least two of the channels with a difference of electric potential applied thereto, said potential applying a driving force to molecules having a net electric charge of either sign, thereby moving said molecule from one channel to another. The extent of the separation will be influenced by the distance the charged molecule must travel to reach the recipient stream. In a preferred embodiment, a very thin (less than 1 millimeter) central channel is sandwiched between two parallel contiguous channels and separated therefrom by two membranes permeable to the appropriate molecules. Each of the recipient channels contains an electrode. The electric field extends from the first recipient channel, across the first membrane, across the small dimension of the central channel, across the second membrane, to the electrode in the second recipient channel. All of the charged molecules will tend to move out of the central channel in response to the electric field. A loss of ions may alter the composition of the mixture in the central channel adversely. For example, the ionic strength or pH may change so much as to disrupt certain bonds. By providing an ion containing stream on either side of the central channel, a charged particle from one recipient channel will tend to enter the central channel for every particle of like charge which leaves the central channel for the opposite recipient channel. This tends to stabilize the composition of the central channel fluid. The flow rate through the recipient channels may be much greater than through the central channel to provide a surplus of ions and to wash away received molecules that have migrated across the membranes by electric forces or dialysis. Dialysis takes place independent of electric forces. The length of said central channel may be very great relative to the distance between membranes so that molecules are exposed to the electric force for a prolonged period, and the distance they must migrate is short.

Amphoterism is a property of amino acids, polypeptides, proteins (of which enzymes are a class), and many other clinically important constituents of body fluids. Ampholytes (amphoteric electrolytes) dissociate both as acids and as bases depending upon the pH of the solution. If an ampholyte in solution is placed in an electric field, the molecules will migrate to one electrode or the other in accordance with the pH of the solution. At a given pH, the molecule behaves neither as an acid nor as a base and does not migrate to anode or cathode. This is called the isoelectric point. It is usually expressed in terms of the pH of the solution at which this occurs. In the isoelectric state the ampholyte is though to be dissociated both as an acid and as a base and fails to appear electrically charged because its positive and negative charges are equal i.e. net charge is zero. When acid is added the ampholyte behaves as a base with a net positive charge; when alkali is added, it behaves as an acid with a net negative charge.

It is an object of the present invention to control and select the migration and separation of different molecules by adjustment of the pH of the streams moving through the electroextraction means. It is a further object of the present invention that means be provided to analyze a pleurality of different molecules simultaneously using a pleurality of said electroextraction means and serial adjustment of pH of the moving streams.

It is an object of the invention that simple detection means be provided for the quantitation of concentration of certain molecules in the separated streams. It is an object of the invention to provide a novel detector incorporating an integrated optical flow path for the simultaneous measurement of multiple separated fluid streams. It is an object of the invention to provide improved laminated photometric apparatus for the analysis of one or more moving fluid streams by measurement of the change in optical properties with time. It is a further object of the invention to provide a wide dynamic range for kinetic enzymatic analysis by repetitive measurement of the same portion of solution at progressively increasing time intervals. It is a further object of the invention to provide means to conserve components of solutions for analysis by maintaining fluid streams at low temperatures during preliminary processes such as pumping and mixing and employing special means to heat the stream abruptly just before measurement begins. It is an object of the invention to provide simple inexpensive sampling and dispensing apparatus providing: cold storage of reagents; dispensing sample and reagent only as needed; controlled washing; changeover from one analysis to another by a single motion.

The foregoing and other objects of the present invention will be described more fully in the following detailed descriptions of the invention.

BRIEF DESCRIPTION OF THE DRAWINGS

FIG. 5 is a schematic drawing of apparatus of the type to which the invention relates showing sample, reagent and multiple buffers being aspirated into an automatic serum protein electrophoretic analyzer with a first electroseparation stage providing a preliminary division and two secondary electroseparation stages each dividing the preliminary division into three parts. All six fractions are shown mixing with color developing reagent and passing through optical detection means for quantitation.

FIG. 8 A,B,C show sample and reagent dispensing and storing means.

DESCRIPTION OF THE PREFERRED EMBODIMENT

Figure 1:
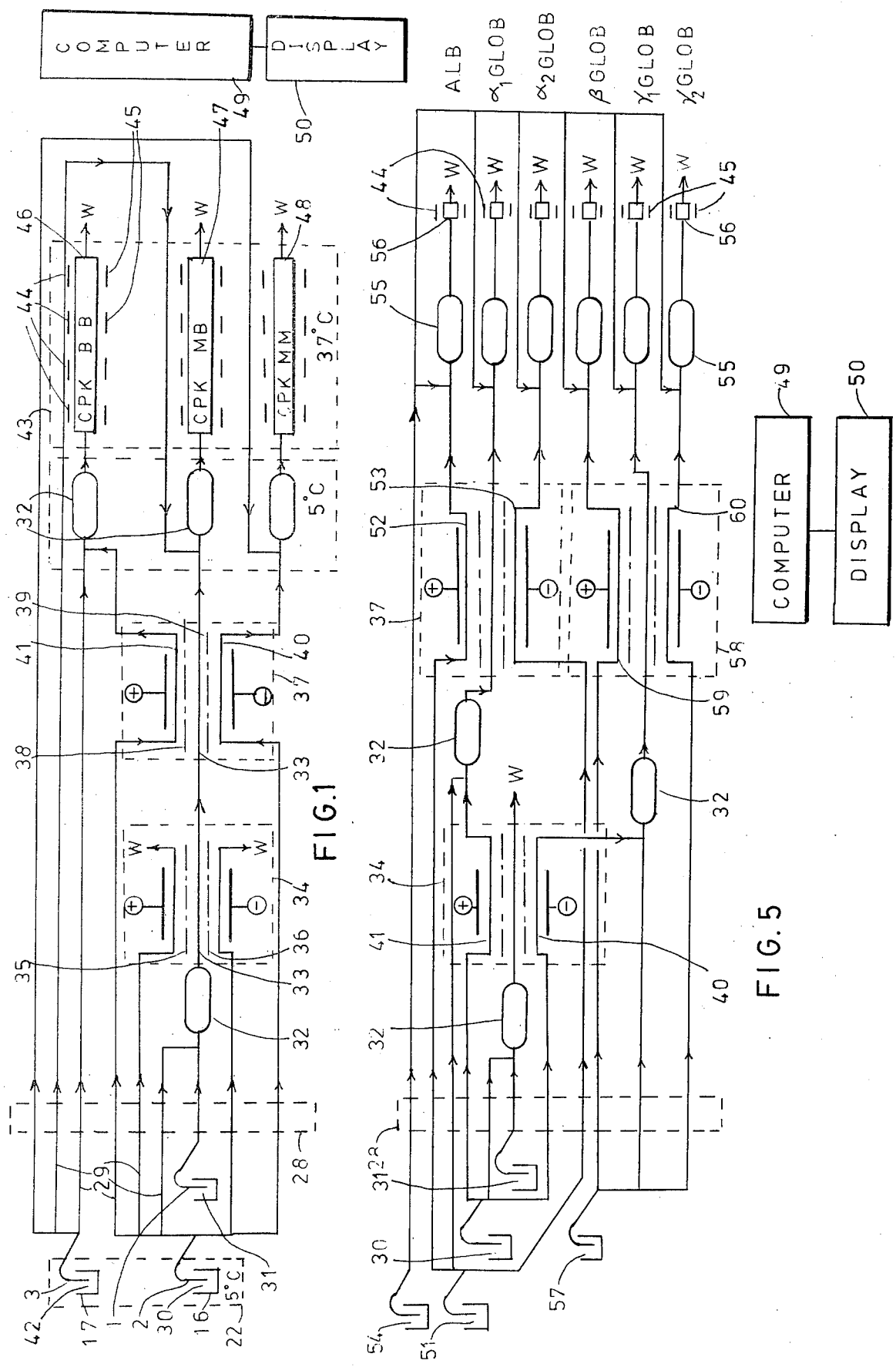
FIG. 1 is a schematic drawing of apparatus of the type to which the invention relates showing sample, buffer and reagent being aspirated into an automatic isoenzyme analyzer with a first electroseparation stage removing interfering agents, a second electroseparation stage separating CPK into MM, MB and BB fractions, color development with reagent, and serial optical measurement of color developing in each separated stream.

Referring first to FIG. 1, peristaltic proportioning pump means 28 pulls fluid at precise rates through flexible tubing lines 29 metering the fluids. Three of these lines terminate in sample pipet 1, buffer pipet 2, and reagent pipet 3, shown immersed in their respective liquids in individual containers. Reagent container 17 and buffer container 16 are held at reduced temperature, by temperature control means 22. Isoenzyme analysis is carried out by addition of buffer 30 to the sample 31 and mixing in mixing coil 32. This adjusts sample pH to the isoelectric point of the CPKMB fraction just before it moves through the central channel 33 of first separation means 34. Membranes 35 and 36 are of a pore size too small to allow passage of the enzymes. Charged molecules small enough to pass through the membranes 35 and 36 are removed by the electrophoretic process and by dialysis which also can remove uncharged molecules at a reduced rate. This process improves final analysis by removal of interfering materials. This partially purified stream enters central channel 33 of second separation means 37 at the isoelectric point of CPKMB. At this pH, the MM fraction is positively charged and migrates toward the cathode. The BB fraction is negatively charged and migrates toward the anode. Membranes 38 and 39 are of a porosity great enough to allow passage of enzyme MM into recipient channel 40 and BB into recipient channel 41. The MB fraction passes through the central channel. Color forming enzyme substrate reagent 42 is pumped and mixed with each of the three separated streams in mixing coils 32 maintained at low temperature to reduce substrate depletion during mixing. The three mixed, cooled streams of enzyme and substrate next enter temperature controlled (37° C.) three channel optical detector 43 wherein optical properties, and change of optical properties with time are detected by light sources 44 and light sensors 45. These view the streams 46, 47 and 48 at progressively later times after mixing of enzymes with substrate and raising to reaction temperature. Signals from the sensors are connected by wires not shown to data processing means 49 where enzyme levels of each fraction are computed and displayed on display means 50. For clarity and simplicity the foregoing description has been limited to one analysis. Additional enzymes or isoenzymes may be analyzed simultaneously by the use of parallel analysis streams. They may share a common detector and data processor, and when isoelectric points are compatible, may even share a separation means.

Figure 2:
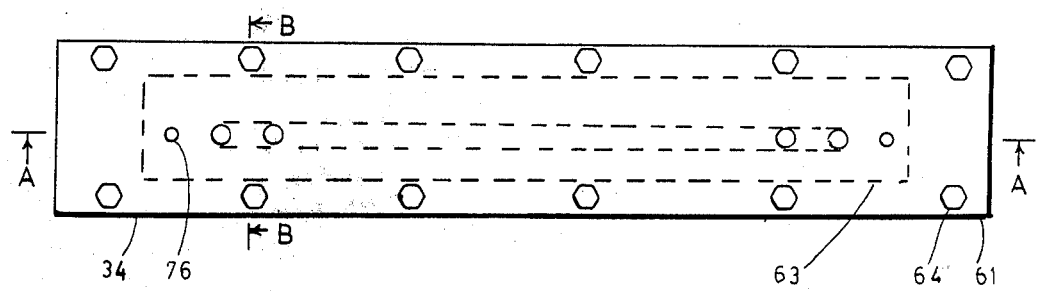
FIG. 2 is a top plan view of the electric separation apparatus.
Figure 3:
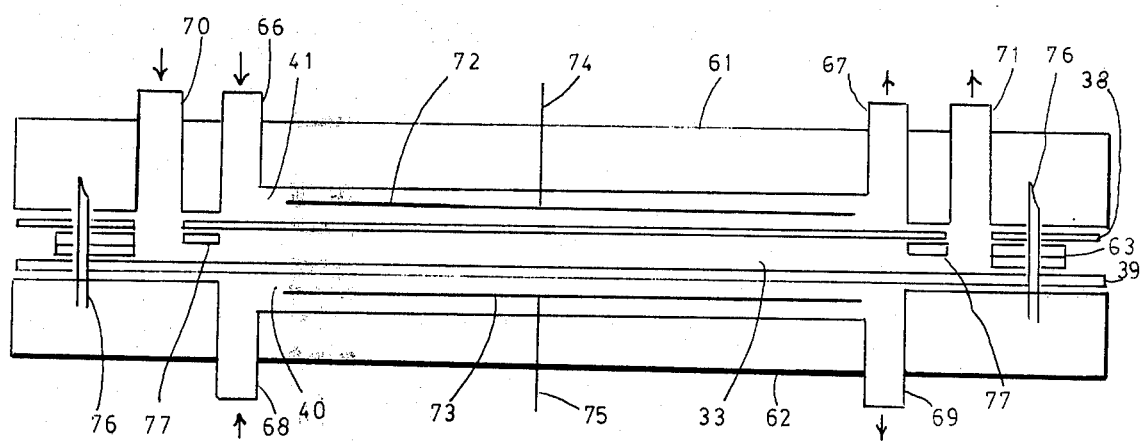
FIG. 3 is a sectional view, taken on line A—A' of FIG. 2.
Figure 4:
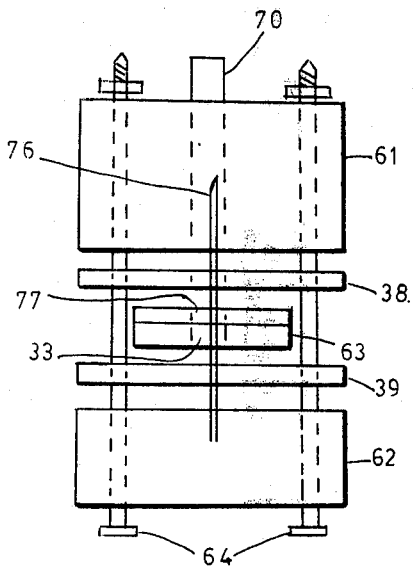
FIG. 4 is a sectional view, taken on line B—B' of FIG. 2.

FIG. 2 shows a plan view of an embodiment of the electric separation apparatus, FIG. 3 is a sectional view taken on line A—A' of FIG. 2 and FIG. 4 is a sectional view taken on line B—B' of FIG. 2. Rigid and thick upper member 61 and lower member 62 and thinner center member 63 are bolted together with bolts 64 sandwiching in thin membranes 38 and 39. These drawings are not to scale. Center member 63 and membranes 38 and 39 are shown much thicker than they are for clarity. Upper member 61 has groove 41 on its underside terminating at tubes 66 and 67. Member 62 has groove 40 on its upper surface terminating in tubes 68 and 69. Center member 63 has slot which connects with tubes 70 and 71 in upper member via 2 holes in membrane 38. When membranes 38 and 39 are tightly compressed by bolts 64, the grooves and slots are sealed so that three parallel channels 33 are formed through which fluid may be passed. The central channel terminates at reagent mixture inlet 70 and outlet 71. Membrane 38 forms a common wall that channel 33 shares with upper channel 41 and membrane 39 forms a common wall that channel 33 shares with lower channel 40. Upper channel 41 terminates in recipient inlet 66 and outlet 67. Lower channel 40 terminates in recipient inlet 68 and outlet 69. Electrode 72 in channel 41 and electrode 73 in channel 40 are connected to positive wire 74 and negative wire 75 respectively. The exact nature of the applied difference of potential may be varied to suit requirements. In the assembly of separator 34, sharp pointed locator pins 76, fastened to lower member 62 transfix membranes 38 and 39 and pass thru holes in upper and center members to facilitate alignment and hold components during assembly. Bolts 64 have sharpened points which pierce membranes during insertion to prevent membrane displacement. After bolting, holes are punched in membrane 38 thru inlet 70 and outlet 71. During operation of the separator it was noted that leakage occurred between recipient stream and reagent mixture stream where inlets 70 and 66 meet membrane 38. Construction of center member 63 was then modified to provide the 2 bridges 77 between inlets 70 and 66 and outlets 67 and 71. This was easily accomplished by constructing the center member of a top and a bottom piece laminated together. The bottom piece has a slot cut between holes in membrane at 70 and 71. The top piece has holes cut at 70 and 71 and a slot cut between 66 and 67, leaving bridges 77 to seal the membrane at these points. A mixture is forced thru central channel 33 via tube 70 (arrows indicate fluid flow). Appropriate recipient fluids such as conductive buffers are passed thru channels 41 and 40 via tubes 66 and 68. A difference of electrical potential is applied to electrodes 72 and 73 via 74 and 75. Charged molecules will migrate toward one of the electrodes as the mixture passes thru channel 33. Larger molecules will migrate more slowly than smaller molecules. Membranes will be selected of a porosity to be freely permeable to the molecules to be removed from central stream but to stop or retard charged molecules which must not leave. Appropriate selection of voltage, pH, ionic strength and flow rate of solutions will regulate separation of molecules so that some will emerge from tube 71 and others from either tube 67 or 69. Either or all streams may then be collected for subsequent measurement or passed thru detectors for immediate measurement. This is but one embodiment of the invention. The channels may be formed in other ways or convoluted. There may be only a single membrane with one electrode within the donor stream, and one in the recipient stream. Two electrodes with two membranes allows the donor stream to gain as many charges as it loses, maintaining its composition and avoiding electrode effects. Air segmentation may be maintained throughout.

Figure 6D:
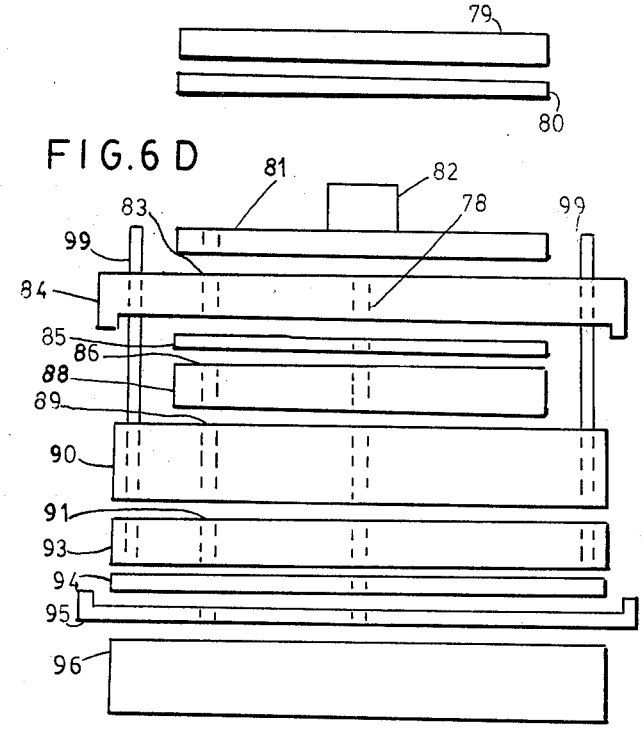
FIG. 6 A,B,C,D show details of an integrated optical detector for kinetic measurement of multiple temperature controlled streams at multiple time intervals.
Figure 6A:
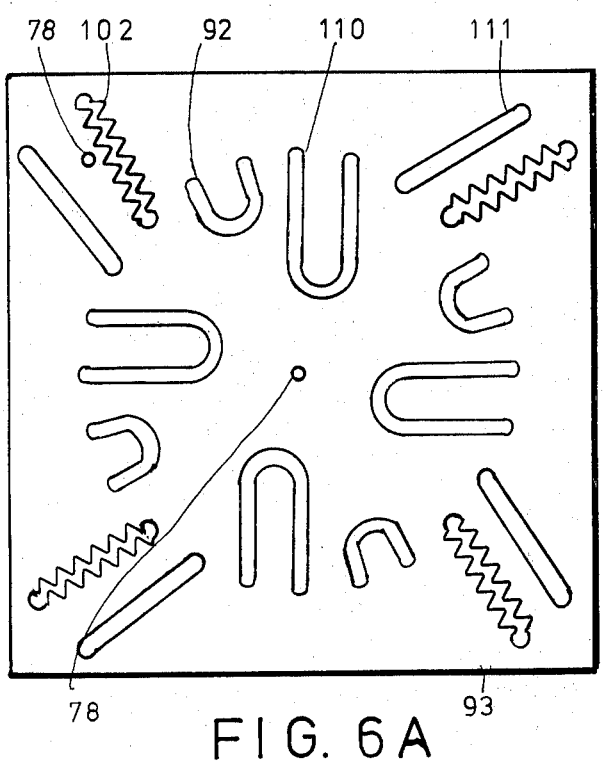
Figure 6B:
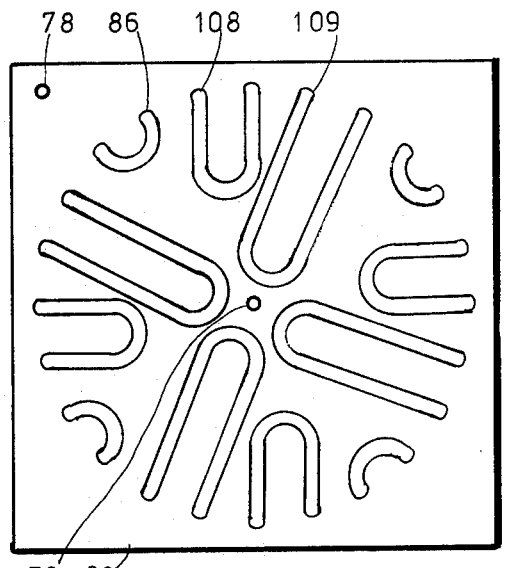
Figure 6C:
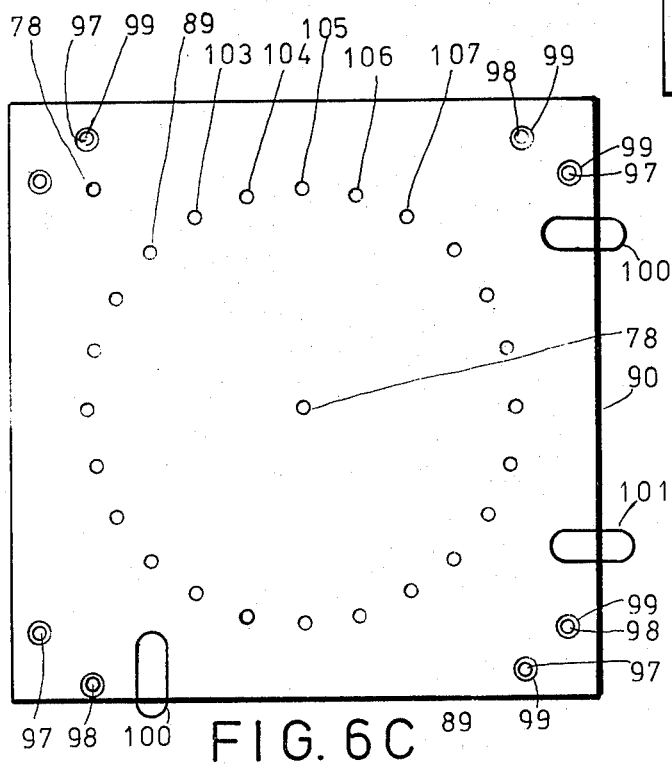

FIG. 5 shows a schematic drawing of an embodiment of the present invention for analyzing multiple molecular forms of compounds such as the analysis termed "serum protein electrophoresis". Peristaltic pump 28 of the tube pinching type in common use aspirates sample 31 and first buffer 30. They mix in mixing coil 32 bringing serum to an intermediate pH at which it enters first separator 34. The negatively charge proteins Albumin, alpha 1 globulin, and alpha 2 globulin enter anode recipient channel 41, and that stream is next mixed in mixing coil 32 with buffer 51 to reach the isoelectric point of alpha 1 globulin. This mixture passes into central channel of separator 37. Albumin, being negatively charged at this pH passes into anode channel 52. Alpha 1 globulin, having no net charge passes directly through the central channel. Alpha 2 globulin, being positively charged at the pH passes into cathode channel 53. These three streams are each combined with color developing reagent 54 in heated mixing coils 55 and then pass through optical detectors 56. The positively charged proteins, beta globulin, gamma 1 globulin, and gamma 2 globulin in first separator 34 enter cathode recipient channel 40. They are then mixed in mixing coil 32 with buffer 57 to reach the isoelectric point of gamma 1 globulin. This mixture next passes into the central channel of separator 58. Beta globulin, being negatively charged at this pH passes into anode channel 59. Gamma 1 globulin passes directly through central channel since it has no net charge. Gamma 2 globulin, being positively charged at this pH, passes into cathode channel 60. All three streams are each combined with a color developing reagent 54 in mixing coils 55 and pass through optical detecting means 56 to measure amount of color which is related to concentration of protein. Seventh and eighth streams not shown may combine buffers 51 and 57 with color reagent 54 in mixing coils and later pass through optical detection means to provide reagent blank values to aid in computation of results. Connecting means not shown connect optical detecting means to data processing and display means 49, 50 wherein signals from detection means are used to compute and display results of the measurement automatically. Optical detectors are indicated as individual filtered light sources 44. Transparent cells 56 and light sensors 45. A second filter may be employed between sample and sensor for fluorescence detection. Any of the optical density or fluorescent detectors well known in the art may be used or a novel single intergrated multipath detector of the type disclosed in FIG. 6 may be employed. In an alternate embodiment not shown, liquid streams may be joined by an air stream. Air introduced concomitantly with the flow of liquids divides the liquid stream into a segmented liquid stream composed of alternate segments of liquid and air. In the course of travel of this stream, the segments of air and the surface tension of the air/liquid interfaces displace liquid from the inner surface of the fluid channel so as to prevent or substantially reduce the mixing of the samples with each other and hence prevent or reduce the contamination of one sample by another in the operation of the invention for analyzing a series of samples or standards. FIG. 6 shows structural details of an optical detector for measuring four temperature controlled flowing fluid streams at six serial time intervals after mixing and temperature adjustment. Other numbers of streams and holes may be employed as required by the particular application. FIG. 6D is a diagrammatic side view of the assembled components. For clarity, the components are not to scale and are not drawn tightly together so as to be leak proof as they would be in normal operation by bolts through locator holes 78. Uniform light source 79 illuminates filter 80 to select particular wavelength of light to pass through rotating occulter 81, which is an opaque disc driven by stepping motor 82 with at least one small opening for light to pass through a hole 83 in opaque clamp mask 84. Light then travels through flat transparent plate 85 of an inert material such as quartz. It then passes through hole 86 which is actually part of a slot 87 in flat plate 88. It then passes through hole 89 in metal plate 90. It next passes through hole 91 which is actually part of slot 92 in flat plate 93. Light then passes through flat transparent plate 94. It then passes through a hole in opaque clamp mask 95, whereupon it impinges upon light sensing means 96, either directly or through directing means such as lenses or mirrors. In the event fluorescence is being measured, a second filter is interposed between fluid cell and sensing means. Filter changing means may be provided to increase the versatility of the device. The foregoing description followed the light path through a single hole. For clarity only this single optical cell out of the twentyfour is shown in FIG. 6D. Multiple light paths are provided to sequentially view and measure the contents of the four moving fluid streams at successive time intervals after mixing and temperature adjustment. The stepping motor 82 positions the occulter 81 so that only a single light path is illuminated at any one time. As motor steps, each light path is viewed in turn. A single light source and sensing means thereby serves multiple light paths and multiple fluid streams by a time sharing approach. A computer clock pulse can trigger the stepping motor and also sample and hold and analog to digital converter means at the signal output of light sensor means, thereby allowing a single signal path to serve all the elements for additional economy. A single switch means on the occulter provides light path location information to the computer once each revolution so that signals will be correctly synchronized. FIG. 6C is a plan view of flat metal plate 90 which is of a thermally conductive metal such as copper. It has the two locating holes 78 in common with other detector components to aid in alignment and assembly. The circular row of holes 89 form the cylindrical bodies of the optical flow cells. Inlet holes 97 and outlet holes 98 have metal tubes 99 projecting from their tops, better seen in side view of FIG. 6D. These tubes may have their inside bores rifled to create a swirling motion in fluid moving therein to promote heat transfer and mixing. An accessory heating means, not shown, may be connected to inlet tubes at a higher temperature to promote more rapid thermal equilibrium of the incoming fluid. The above holes all pass through from top to bottom of the plate and may be coated inside with a non reactive material such as gold plating. Heating elements 100 and temperature sensor 101 are connected to control means not shown to maintain plate 90 at the desired reaction temperature. FIG. 6B is a plan view of upper flat plate 88, and FIG. 6A is a plan view of lower flat plate 93. These are made of thin, hard inert material such as Corning Fotoform or Fotoceram. These are opaque glassy materials that can be machined by a photographic exposure and chemical etch to provide fine, detailed, intricate holes, grooves and slots without high labor costs. The various shaped slots go through from top to bottom faces of the thin plates. They form the side walls of fluid channels connecting the various holes in metal plate 90. The top and bottom walls of the channels are formed by one of the transparent plates 85 or 94 and either the top or bottom face of metal plate 90. Only the metal plate is thermally conductive, the other walls are insulating, therefor heat transfer is with the metal plate. First slot 102 in plate 93 is convoluted to provide improved mixing and heat transfer to incoming fluid. It connects inlet tube 99 to first optical cell hole 89, and incoming fluid must be thermally equilibrated promptly. Fluid proceeds up hole 89 in metal plate 90 to slot 86 in plate 88. This carries it to second hole 103 in metal plate. It goes down this hole to slot 92 in bottom plate 93, which carries it to third hole 104 in metal plate. It goes up hole to slot 108 in plate 88 which carries it to fourth hole 105 in metal plate. It goes down this hole to slot 110 in plate 93, which carries it to fifth hole 106 in metal plate. It goes up this hole to slot 109 in plate 88, which carries it to sixth hole 107 in metal plate. It goes down this hole to slot 111 in plate 93 which carries it to outlet tube 99 in metal plate. As the fluid proceeds from the first to the sixth hole it will be noted that the connecting channels formed by the slots in plates 88 and 93 become longer and longer. This provides progressively longer time intervals between optical readings. This non linear sampling method allows a wide range of sensitivity and multiple samplings for reading the proper part of the dynamic enzyme curve while the actual light readings are made at uniform time intervals.

Figure 7A:
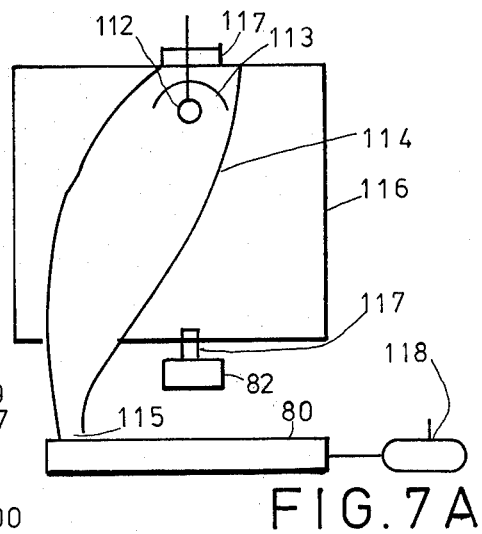
FIG. 7 A,B show light sources for optical detector.
Figure 7B:
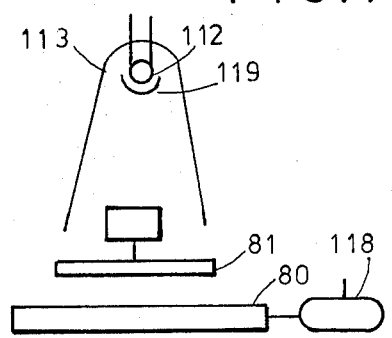

FIG. 7A shows a rotating light source for the optical detector. Fixed light emitter 112 is backed by a fixed reflector 113. Mirrored chamber 114 has a small eccentric outlet 115 through which a concentrated beam of light passes. The chamber is contained within cylinder 116 mounted on bearings 117. The cylinder and mirrored chamber are rotated by stepping motor 82 to illuminate each hole in sequence. No occulter is required. Filter 80 may be changed by rotary solenoid 118. FIG. 7B shows a simple light source for use with occulter 81. Fixed light emitter 112 has both a fixed back reflector 113 and a fixed front reflector 119 so placed as to provide an annular beam of light falling on all holes uniformly, but shielded from all holes except one by occulter means 81. Filter 80 may be changed by rotary solenoid 118.

FIG. 8A shows a side view of a sample and reagent dispensing means for providing input fluids into the analyzer. Tubing lines from peristaltic pump terminate at aspiration pipets for sample 1, buffer 2, and reagent 3. These project below support plate 4 which also supports pulleys 5. Support plate 4 is suspended above base plate 6 by two vertical guide rods 7 and two sloping guide rods 8. Container carrier 9 is slideably connected to vertical guide rods 7 which pass through holes 10 in carrier. FIG. 8B is a plan view of said carrier. Turntable 11 rotates about bearing 12 mounted in carrier 9. Said turntable is hand rotatable to one of four positions fixed by detent 13 and notches 14. Sample container is held by spring fingers in center hole 15 designed to accomodate a wide variety of containers. Sample container remains unchanged by any rotation of the turntable. When carrier 9 is raised to the support plate, sample pipet 1 will enter said sample container, because guide rods restrict movement of carrier to the vertical. In each of the four rotational positions of said turntable, a different set of one buffer container 16 and one reagent container 17 are positioned under their respective pipets. When the carrier 9 is raised to the upper position, these pipets 2 and 3 will enter their containers and aspirate their contents. Each of the four rotational positions of said turntable and each set of containers is used for a different enzyme analysis. One position and container set may be used for CPK analysis and another for LDH. A third may be used for phosphatase analysis. A window 18 in the side of carrier 9 displays the selected analysis to the operator. In addition a row of four analysis selecting switches 19, one for each selected analysis is mounted beneath support plate 4. This is shown in underside detail of plate 4 in FIG. 8C. Each one of said switches represents a different analysis. When actuated, the switch communicates to the computer which of the four sets of containers is being aspirated so that the computer can select the appropriate operating program. It may also begin an aspiration timer to signal when it has had enough fluid for an adequate sample. On the periphery of said turntable are mounted four position indicating fingers 20. They are so located that one of them will actuate the appropriate one of the four analysis selecting switches when carrier is in aspirate position. This eliminates operator effort and error. To further reduce operator error, each container hole 21 in said turntable is of a different shape. The outside of each container is shape coded so that it can fit into only the correct hole. The sensitive reagents employed in these analyses often deteriorate rapidly at room temperature. In order to maintain an instrument ready at all times, and reduce operator labor, this invention provides reagent cold storage means for reagents in operating position. This also provides means for mixing reagents with enzymes at reduced temperature to avoid substrate depletion before measurement. Refrigeration means 22 cools metal plate 23 in base plate. Base of turntable is a thermally conductive block 24 which rests upon cold plate 23 cooling containers which rest in holes in said block 24. For ease of fabrication the holes may be round and a thin plate with special shape coded holes cut therein fastened to the top. The carrier may be insulated. To reduce the carryover from one sample to the next, a washing and air segmentation step is provided by wash carrier 25 which slides up and down sloping guide rods 8 fitting in holes 10 in said carrier. In the uppermost position against support plate 4, all aspirating pipets are immersed in wash liquid and wash liquid is pumped through all lines, purging them of preceeding sample. In this position, said carrier actuates wash timer switch 26. When washing is complete, the operator is signalled. A cable 27 runs from reagent carrier 9, around the two pulleys 5 to wash carrier 25. It is of such a length that when one carrier is in aspirating position, the other rests on the base plate. Reagent carrier 9, being heavier, will rest on base plate when the instrument is unattended, leaving it in wash mode while operator inserts another sample, selects analysis or performs unrelated duties. When reagent carrier is lifted by hand to aspirate position, wash carrier falls to base plate. Operator must hold the carrier in this position until signalled cycle is complete, whereupon operator lowers it. This method consumes valuable reagent only as needed. Every time a carrier is lowered, a bubble of air is aspirated. This air segmentation contributes to wash process. When a large number of samples are to be analyzed at one time, any of the automatic sampling devices in common use or the one described in the copending parent application may be employed.

By changing electroseparator voltage, reversing it or applying diverse voltage waveforms, changes in the properties of the analyzer may be accomplished by a simple computer instruction. For example, apparatus of FIG. 5 may be made to measure reagent blanks by removing voltage from first electroseparator.

While I have shown and described the preferred embodiments of my invention, it will be understood that the invention may be embodied otherwise than as herein specifically illustrated or described, and that certain changes in the form and arrangement of parts and in the specific manner of practicing the invention may be made without departing from the underlying ideas or principles of this invention within the scope of the appended claims.

What is claimed is:

1. Laminated optical apparatus for photometric analysis of fluid in a moving stream comprising: upper transparent plate means; lower transparent plate means; opaque center plate means having a plurality of holes therethrough, said holes providing passages for said moving fluid and also providing the lateral walls of a series of optical measuring cells; fluid inlet means for admitting said moving fluid stream into said optical apparatus for measurement of the optical properties of said fluid, said fluid inlet means being fastened into one of said holes in said center plate means; fluid outlet means for removal of said moving fluid stream from said cells after said measurement, said fluid outlet means being fastened to one of said holes in said center plate means; thin plate means disposed on both sides of said center plate means between said upper transparent plate means and the upper face of said center plate means on one side and between said lower transparent plate means and the lower face of said center plate means on the other side, said thin plate means having shaped slots, said slots in combination with the faces of said transparent plate means and the faces of said center plate means forming fluid flow channels connecting said fluid inlet means, said fluid outlet means, and said holes in said center plate means, thereby providing a continuous fluid flow pathway from said fluid inlet means through a series of optical measurement cells to said fluid outlet means, said optical measurement cells being formed by said upper and lower transparent plate means serving as common end windows and said holes in said center plate means and said slots in said thin plate means serving as individual tubular optical cell bodies; upper mask clamp plate means and lower mask clamp plate means positioned against upper transparent plate means and lower transparent plate means respectively, said clamp plate means being opaque and rigid and having holes therethrough to register with corresponding optical measurement cells for passage light, with additional holes for positioning and clamping bolt means for clamping all the aforesaid plate means together in a fluid and light tight manner, thereby facilitating assembly and disassembly for cleaning; light source means disposed on one side of said optical cells; light measuring means disposed on another side of said optical cells; and data processing means connected to said light measuring means to process light measurement information into useful form.

2. The invention of claim 1 further comprising temperature adjusting means to adjust rapidly a cool entering fluid up to a warmer temperature at which more useful optical measurements such as enzyme kinetics can be performed, while maintaining cool temperature in said fluid during preliminary operations such as mixing to conserve materials prior to measurement including: said fluid inlet means of a thermally conductive material in thermal contact with said center plate means; said center plate means of a thermally conductive material; thermal means connected to said center plate means to maintain said center plate means and said fluid inlet means and fluid passing therethrough at desired temperature.

3. The invention of claim 2 further comprising rifling of the inner bore of said fluid inlet means to enhance mixing and heat transfer to entering fluid.

4. The invention of claim 2 further comprising separate thermal means connected to said fluid inlet means to enhance heat transfer to entering fluid.

5. The invention of claim 2 further comprising convolutions of said slot in said thin plate means forming fluid flow channel between said fluid inlet means and said first optical cell to enhance heat transfer to entering fluid.

6. The invention of claim 1 wherein said series of optical measuring cells are disposed in a circle so that a rotating beam of light means will illuminate each cell in turn.

7. The invention of claim 6 wherein said optical cells are generally uniformly spaced from one another so that a rotating beam of light, when rotating at a uniform rate, will illuminate each cell in turn at regular and generally uniform time intervals.

8. The invention of claim 7 wherein said slots in said thin plate means providing fluid flow pathways between said individual optical cells are of different length or volumes, thereby providing non uniform time intervals between the appearance of a portion of moving fluid in each successive optical cell while actual light measurements are made at uniform time intervals.

9. The invention of claim 8 wherein said non uniform time intervals of appearance of a portion of fluid between said optical cells are progressively longer from first to last of said optical cells to provide a wide dynamic range for kinetic measurements.

10. The invention of claim 6 wherein said rotating beam of light means includes: stationary light source means; rotating occulting means, said occulting means providing illumination of one of said optical cells at a time.

11. The invention of claim 6 wherein said rotating beam of light means comprises: stationary light source means; and rotating eccentric light directing means, said light directing means illuminating one of said optical cells at a time.

12. Photometric apparatus for analysis of the change of optical properties with time of a fluid comprising: a series of optical cells disposed in a generally circular pattern so that a rotating beam of light will illuminate each cell sequentially; a rotating uniform beam of light means for illuminating each of said optical cells sequentially; light measuring means for measuring the light leaving each optical cell as a result of said illumination; cell connecting fluid channel means providing a continuous path for fluid to pass into and out of a first said optical cell and into an adjacent cell in series and from that cell into the adjacent cell in series so that each portion of fluid travels around in a generally circular path moving from the first said optical cell to each adjacent optical cell in sequence; fluid inlet means to admit fluid to the fluid channel leading to said first optical cell; fluid outlet means to remove fluid leaving the fluid channel from the last said optical cell in the series; fluid moving means to move fluid to be analyzed through said fluid pathway; wherein said optical cells are constructed generally optically equal and illuminated by the same light intensity so that a difference in light measured by said light measurement means of light leaving each said optical cell in sequence as a particular portion of fluid moves sequentially from cell to cell around the circle will indicate only change in optical properties of said particular portion of fluid with time from entrance to said first optical cell to exit from said last optical cell.

13. The invention of claim 12 wherein the assembly of uniform cell structures comprises a series of plates fastened together in sequence including:

a. upper rigid opaque mask clamp means having holes to admit light to said individual optical cells;
b. upper transparent plate means providing the entrance window for said individual optical cells;
c. upper thin opaque plate means having shaped slots to provide fluid flow channels;
d. center opaque thick plate means having holes therethrough in a generally circular pattern to provide the bodies of said individual optical cells;
e. lower thin opaque plate means having shaped slots to provide fluid flow channels;
f. lower transparent plate means proving the exit windows for said individual optical cells;
g. and lower rigid opaque mask clamp means having holes to pass light from said individual optical cells.

14. The invention of claim 13 further comprising temperature adjusting means to adjust rapidly a cool entering fluid up to a warmer temperature at which more useful optical measurements such as enzyme kinetics can be performed, while maintaining cool temperature in said fluid during preliminary operations such as mixing to conserve materials prior to measurement including: said center plate means of a thermally conductive material; fluid inlet means of a thermally conductive material; thermal means connected to said center plate means and to said fluid inlet means to maintain said center plate means and said fluid inlet means and fluid passing therethrough at desired temperature.

15. The invention of claim 14 further comprising rifling of the inner bore of said fluid inlet means to enhance mixing and heat transfer to entering fluid.

16. The invention of claim 13 further comprising convolutions of said slots in said thin plate means forming fluid flow channels to enhance heat transfer to moving fluid.

17. The invention of claim 13 wherein said slots in said thin plate means providing fluid flow pathways between said individual optical cells are of different lengths or volumes, thereby providing nonuniform time intervals between the appearance of a portion of fluid in each successive optical cell while actual light measurements are made at uniform time intervals with a light beam rotating at a uniform rate and scanning optical cells disposed in a circle at uniform distances form one another.

18. The invention of claim 13 wherein a plurality of fluid streams share a common assembly with each of said fluid streams having its own inlet means, outlet means, fluid flow channels and one or more optical cells; the optical cells of each fluid stream forming a sector of the circle of optical cells.

19. The invention of claim 13 wherein said rotating beam of light means includes: stationary light source means; rotating occulting means, said occulting means providing illumination of one said optical cell at a time.

20. The invention of claim 13 wherein said rotating beam of light means comprises: stationary light source means; and rotating eccentric light directing means, said light directing means illuminating one of said optical cells at a time.

21. The invention of claim 8 wherein a plurality of moving fluid streams share a common laminated optical apparatus with each of said fluid streams having its own inlet means, outlet means, fluid flow channels and one or more optical cells; the optical cells of each fluid stream forming a sector of the circle of optical cells.

* * * * *